United States Patent
Li et al.

(10) Patent No.: US 11,032,975 B2
(45) Date of Patent: Jun. 15, 2021

(54) LIGHT REGULATION METHOD FOR PROMOTING ACCUMULATION OF THC IN CANNABIS PLANTS

(71) Applicant: Fujian Sanan Sino-Science Photobiotech Co., Ltd, Quanzhou (CN)

(72) Inventors: Shaohua Li, Quanzhou (CN); Guojie Liu, Quanzhou (CN); Jian Ma, Quanzhou (CN); Yang Li, Quanzhou (CN); Zhi Wang, Quanzhou (CN); Hengsheng Chen, Quanzhou (CN); Linping Meng, Quanzhou (CN); Shu Jia, Quanzhou (CN)

(73) Assignee: FUJIAN SANAN SINO-SCIENCE PHOTOBIOTECH CO., LTD, Quanzhou (CN)

( * ) Notice: Subject to any disclaimer, the term of this patent is extended or adjusted under 35 U.S.C. 154(b) by 133 days.

(21) Appl. No.: 16/446,602

(22) Filed: Jun. 19, 2019

(65) Prior Publication Data

US 2020/0396907 A1    Dec. 24, 2020

(51) Int. Cl.
| | |
|---|---|
| *A01H 6/28* | (2018.01) |
| *A01G 7/04* | (2006.01) |
| *A01G 9/20* | (2006.01) |
| *A01G 9/26* | (2006.01) |
| *A01G 7/06* | (2006.01) |
| *A01H 3/02* | (2006.01) |
| *F21Y 115/10* | (2016.01) |

(52) U.S. Cl.
CPC .............. *A01G 7/045* (2013.01); *A01G 7/06* (2013.01); *A01G 9/20* (2013.01); *A01H 3/02* (2013.01); *F21Y 2115/10* (2016.08)

(58) Field of Classification Search
CPC ........ A01G 7/045; A01G 3/02; F21Y 2115/10
USPC ......................................................... 47/58.1
See application file for complete search history.

(56) References Cited

PUBLICATIONS

Ajinkya Lalge et al.The effects of red, blue and white light on the growth and development of *Cannabis sativa* L. Mendel Net Nov. 8-9, 2017 Brno Czech Republic.*
Kim Hyeon-Hye et al. Green-light Supplementation for Enhanced Lettuce Growth under Red and Blue light emitting Diodes . HortScience 39(7) 1617-1622 2004.*
Tingting Zhang et al. Green light signaling and adaptive response. Plant signaling & Behavior 7:1, Jan. 1-4, 2012 Landes Bioscience.*
Magagnini et al. The effect of Light Spectrum on the Morphology and Cannabinoid Content of *Cannabis sativa* L. Med Cannabis Cannabinoids ;1:19-27 2018.*

* cited by examiner

*Primary Examiner* — Annette H Para

(57) ABSTRACT

A method for promoting the accumulation of secondary metabolites of *cannabis* is disclosed. The method comprises the step of adding a green-yellow light, which has a peak wavelength at 506-571 nm, into the indoor growing environment for *cannabis*, and maintaining the light intensity and other growth conditions, to improve the content of secondary metabolites. The production of secondary metabolites of *cannabis* can be increased by up to 18%.

14 Claims, 2 Drawing Sheets

LIGHT REGULATION METHOD FOR PROMOTING ACCUMULATION OF THC IN *CANNABIS* PLANTS

TECHNICAL FIELD

The subject matter herein relates to a technical filed of medicinal plants, and in particularly relates to a light regulation method for promoting accumulation of secondary metabolites in *cannabis* plants.

BACKGROUND

*Cannabis* is an annual erect herb. The main active ingredient in *cannabis* plants is cannabinoids. Currently, over 70 kinds of natural cannabinoids are found, which are mainly used in some nervous system diseases, such as multiple sclerosis, motor neuropathy, chronic intractable pain, a drug-induced vomiting. Its main effective pharmaceutical ingredients include tetrahydrocannabinol aid (THCa), cannabidiolic acid (CBDa), cannabinoid acid (CBNa), cannabichromene acid (CBCa), tetrahydrocannabinol (THC), cannabinol (CBN), cannabidiol (CBD) and cannabichromene (CBC). The highly potent ingredients are THC, CBN, CBC, and CBD. Cannabidiol exerts analgesic and anti-inflammatory effects by dual inhibition of cyclooxygenase and lipoxygenase. It has an effect of anti-epileptic, anti-psychotic, anti-depressant, and analgesia. THC can be helpful to regulate the immune system, eliminate inflammation, stimulate appetite, and make patients calm. The development and research of the medicinal value of THC has a broad prospect. Accordingly, it is important to develop the *cannabis* cultivation technology for growing *cannabis* with high medicinal ingredients.

Indoor cultivation of *cannabis* can obtain plant raw materials with stable content and yield of medicinal ingredients. At the same time, the indoor cultivation of *cannabis* can be grown in all seasons and several times a year. The reason ecological factors, including light, temperature, humidity, and nutrition, required for growth is pretty stable indoor. Light is one of the most relevant environmental factors influencing plant behavior. It is not only the basic energy source for photosynthesis, but also an important regulator of plant growth and development, which plays a significant role in plants' morphogenesis, reproductive development, and regulation of secondary metabolites. It is important to control the biosynthesis of its medicinal components by regulating the light quality growing *cannabis*.

SUMMARY

A method for promoting the accumulation of secondary metabolites of *cannabis*, specifically for promoting the accumulation of secondary metabolites of *cannabis*, by adding the green-yellow light having a peak wavelength at 506-571 nm in a growing environment for *cannabis*.

In some embodiments, a ratio of the photon number of the green-yellow light to the photon number of the entire light source does not exceed 50%.

In some embodiments, the light source used in the indoor growing environment for *cannabis* is a LED light source.

In some embodiments, the LED light source is composed of 10-18.4% blue light, 40-73.6% red light, and 8-34% green-yellow light.

In some embodiments, the blue light has a peak wavelength at 440-450 nm, the red light has a peak wavelength at 655-665 nm, and the green-yellow light has a peak wavelength at 506-571 nm. Preferably, the green-yellow light peak wavelength is ranged at 506-523 nm and at 571 nm.

In some embodiments, the green-yellow light peak wavelength lies at 506-523 nm and 571 nm.

In some embodiments, the LED light source comprises 16-34% green-yellow light.

In some embodiments, a ratio of the number of photons of blue light to the number of photons of red light is 1:4.

In some embodiments, the added green-yellow light is from a LED chip or a LED chip coated with phosphor material.

In some embodiments, an initial light intensity is 200 $\mu mol/m^2 s$, a maximum light intensity is 1000 $\mu mol/m^2 s$, and a photoperiod is less than or equal to 14 h/d.

The present disclosure provides a method for promoting the accumulation of secondary metabolites of *cannabis*. By introducing a green-yellow light, which has a peak wavelength at 506-571 nm, into the indoor growing environment for *cannabis*, and maintaining the light intensity and other growth conditions, the production of secondary metabolites of *cannabis* can be increased by up to 18%.

DETAILED DESCRIPTION OF THE INVENTION

Figure 1:
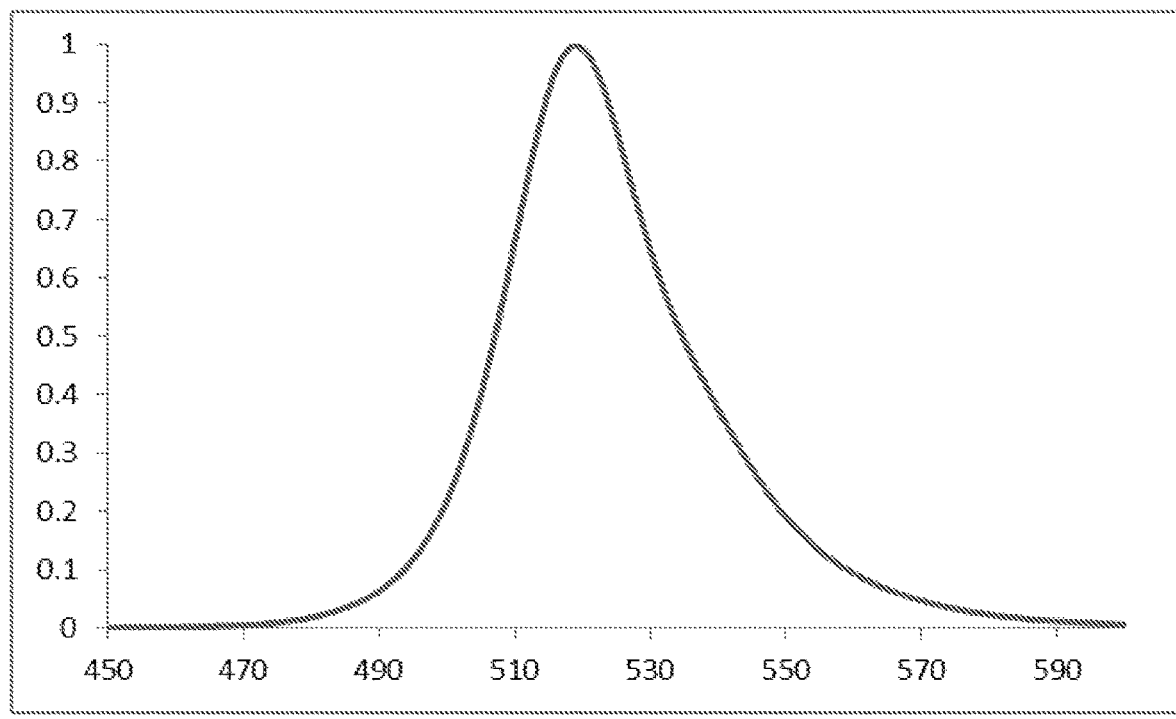
FIG. 1 is a spectral distribution graph from a LED chip.
Figure 2:
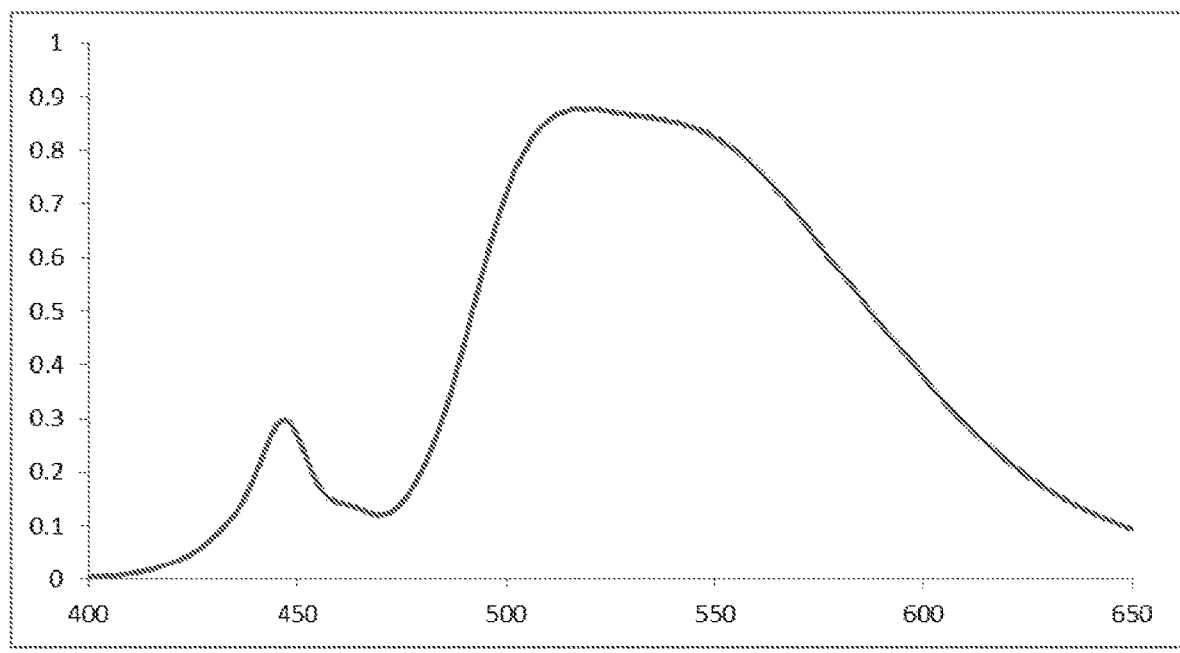
FIG. 2 is a spectral distribution graph from a LED chip coated with phosphor material.

The present disclosure will be further described in detail below with reference to the drawings and specific embodiments, in order to better understand the objective, the technical solution and the advantage of the present disclosure. It should be understood that the specific embodiments described herein are merely illustrative and are not intended to limit the scope of the disclosure.

Embodiment 1

The *cannabis* seedlings with the better roots were transplanted into a substrate or a rock wool. Four plants are placed within one square meter. The ambient temperature was set to T=24-26° C. and the humidity was T=60-70% RH. When the height of plants was about 20 cm, the plants were topped for promoting the growth of lateral branches. When the lateral branches were grown for two weeks, the lateral branches were topped to obtain more lateral branches. After the end of a vegetative growth phase, a flowering treatment was carried out for one week. During the whole growth process, the LED light source was used to provide a growing environment for the plant. The initial light intensity was set to 200 $\mu mol/m^2 s$, and a maximum light intensity could reach 1000 $\mu mol/m^2 s$ with the growth of the plants. The light period was 14 h/d. A control group was set with a blue light having a peak wavelength at 445 nm. Four experimental groups are set with green-yellow light having peak wavelength at 506 nm, 519 nm, 526 nm, and 571 nm. At the time of collecting, the THC in the *cannabis* of the plant was measured and the results are shown in Table 1.

TABLE 1

| Independent Irradiation | Peak Wavelength | THC content (%) |
|---|---|---|
| Control Group 1 | 445 | 21.43 |
| Experimental Group 1 | 506 | 22.86 |
| Experimental Group 2 | 519 | 21.81 |
| Experimental Group 3 | 526 | 23.79 |
| Experimental Group 4 | 571 | 22.15 |

The results suggest that green-yellow light is more effective than blue light in improving the THC content, and up to 11%.

Embodiment 2

The *cannabis* seedlings with the better roots were transplanted into a substrate or a rock wool. Four plants are placed within one square meter. The ambient temperature was set to T=24-26° C. and the humidity was T=60-70% RH. When the height of plants was about 20 cm, the plants were topped for promoting the growth of lateral branches. When the lateral branches were grown for two weeks, the lateral branches were topped to obtain more lateral branches. After the end of a vegetative growth phase, a flowering treatment was carried out for one week. During the whole growth process, the LED light source was used to provide a growing environment for the plant. The initial light intensity was set to 200 µmol/m²s, and a maximum light intensity could reach 1000 µmol/m²s with the growth of the plants. The light time was 14 h/d. A control group was set with a light source comprising 20% blue light and 80% red light, wherein the blue light has a peak wavelength at 445 nm and the red light has a peak wavelength at 660 nm. The experimental groups (Table 2) are formed by adding green-yellow light with different ratio into the control group, and at the same time the photon ratio of the red and blue light is 4:1. At the time of collecting, the THC in the *cannabis* of the plant was measured and the results are shown in Table 2.

TABLE 2

| Combination of Lights | Blue Light (%) | Red Light (%) | Green-Yellow Light (%) | Peak Wavelength | THC content (%) |
|---|---|---|---|---|---|
| Control Group 2 | 20 | 80 | 0 | — | 21.45 |
| Experimental Group 5 | 18.4 | 73.6 | 8 | 526 | 21.92 |
| Experimental Group 6 | 16.8 | 67.2 | 16 | 526 | 22.83 |
| Experimental Group 7 | 15 | 60 | 25 | 526 | 23.38 |
| Experimental Group 8 | 13.2 | 52.8 | 34 | 526 | 24.11 |
| Experimental Group 9 | 10 | 40 | 50 | 526 | 22.71 |

The results suggest that it is possible to improve the THC content, up to 12%, by adding green-yellow light into the combination of blue light and red light with different ratio of green-yellow, is more effect than blue light in improving the THC content.

Embodiment 3

The *cannabis* seedlings with the better roots were transplanted into a substrate or a rock wool. Four plants are placed within one square meter. The ambient temperature was set to T=24-26° C. and the humidity was T=60-70% RH. When the height of plants was about 20 cm, the plants were topped for promoting the growth of lateral branches. When the lateral branches were grown for two weeks, the lateral branches were topped to obtain more lateral branches. After the end of a vegetative growth phase, a flowering treatment was carried out for one week. During the whole growth process, the LED light source was used to provide a growing environment for the plant. The initial light intensity was set to 200 µmol/m²s, and a maximum light intensity could reach 1000 µmol/m²s with the growth of the plants. The light period was 14 h/d. A control group was set with a light source comprising 20% blue light and 80% red light, wherein the blue light has a peak wavelength at 445 nm and the red light has a peak wavelength at 660 nm. The experimental groups (Table 3) are formed by adding green-yellow light with fixed ratio and different peak wavelength into the control group, and at the same time the photon number ratio of the red light and blue light is 4:1. At the time of collecting, the THC in the *cannabis* of the plant was measured and the results are shown in Table 3.

TABLE 3

| Combination of Lights | Blue Light (%) | Red Light (%) | Green-Yellow Light (%) | Peak Wavelength | THC content (%) |
|---|---|---|---|---|---|
| Control Group 3 | 20 | 80 | 0 | — | 21.78 |
| Experimental Group 10 | 16.4 | 65.6 | 18 | 506 | 25.52 |
| Experimental Group 11 | 16.4 | 65.6 | 18 | 511 | 25.21 |
| Experimental Group 12 | 16.4 | 65.6 | 18 | 516 | 25.85 |
| Experimental Group 13 | 16.4 | 65.6 | 18 | 519 | 25.11 |
| Experimental Group 14 | 16.4 | 65.6 | 18 | 523 | 24.92 |
| Experimental Group 15 | 16.4 | 65.6 | 18 | 526 | 23.93 |
| Experimental Group 16 | 16.4 | 65.6 | 18 | 535 | 23.98 |
| Experimental 17 | 16.4 | 65.6 | 18 | 571 | 25.06 |

The results suggest that by adding 18% green-yellow light into the combination of red light and blue light, treatment with different peak wavelength will affect the THC content in the *cannabis*, and up to 18%.

It can be seen from Table 1 that in the environment with the same growth conditions and light intensity, adding light which has a peak wavelength at 506-571 nm helps to improve the THC content in the *cannabis*. When the added light takes a ratio at 18% and has a peak wavelength at 516 nm, the result is preferable, and increases by 18% than the control group 3.

It should be noted that the aforementioned embodiments are merely preferred embodiments of the present disclosure, and those embodiments are not to be deemed as limiting the scope of the invention. The scope of the disclosure should be limited by the by the scope of the claims. It will be apparent to those skilled in the art that other modifications and changes may be made without departing from the spirit and scope of the disclosure.

What is claimed is:

1. A method for promoting the accumulation of THC (tetrahydrocannabinol) in *cannabis*, comprising:

adding a green-yellow light into an indoor growing environment for *cannabis* to improve the accumulation of the THC, wherein the green-yellow light has a peak wavelength at 506-571 nm.

2. The method of claim 1, wherein the step of adding the green-yellow light which has the peak wavelength at 506-571 nm into the growing environment for *cannabis* further comprises an independent irradiation or a combination irradiation with other lights.

3. The method of claim 2, wherein in the combination irradiation with the other lights, a ratio of the green-yellow light photon number to an entire light source photon number is less than or equal to 50%.

4. The method of claim 1, wherein the light source used in the indoor growing environment for *cannabis* is a LED light source.

5. The method of claim 4, wherein the LED light source comprises 10-18.4% blue light, 40-73.6% red light, and 8-34% green-yellow light.

6. The method of claim 4, wherein the blue light has a peak wavelength at 440-450 nm, the red light has a peak wavelength at 655-665 nm, and the green-yellow light has a peak wavelength at 506-571 nm.

7. The method of claim 5, wherein the green-yellow light peak wavelength is 506-523 nm and 571 nm.

8. The method of claim 4, wherein the LED light source comprises 16-34% green-yellow light.

9. The method of claim 4, wherein a ratio of a blue light photon number to a red light photon number is 1:4.

10. The method of claim 1, wherein the green-yellow light is from a LED chip or a LED chip coated with phosphor material.

11. The method of claim 3, wherein in the indoor growing environment for *cannabis*, an initial light intensity is 200 μmol/m$^2$s, a maximum light intensity is 1000 μmol/m$^2$s, and a photoperiod is less than or equal to 14 hid.

12. The method of claim 2, wherein the light source used in the growing environment for *cannabis* is a LED light source.

13. The method of claim 5, wherein the LED light source comprises 16-34% green-yellow light.

14. The method of claim 6, wherein the LED light source comprises 16-34% green-yellow light.

* * * * *